United States Patent
Niimoto et al.

(10) Patent No.: US 7,432,396 B2
(45) Date of Patent: Oct. 7, 2008

(54) PROCESS FOR PRODUCING (Z)-1-PHENYL-1-DIETHYLAMINO CARBONYL-2-HYDROXYMETHYL CYCLOPROPANE

(75) Inventors: Yoshihide Niimoto, Kobe (JP); Hiroharu Kumazawa, Takatsuki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/630,344

(22) PCT Filed: Jun. 23, 2005

(86) PCT No.: PCT/JP2005/012020

§ 371 (c)(1),
(2), (4) Date: Dec. 21, 2006

(87) PCT Pub. No.: WO2006/001498

PCT Pub. Date: Jan. 5, 2006

(65) Prior Publication Data
US 2007/0249864 A1    Oct. 25, 2007

(51) Int. Cl.
*C07C 233/00* (2006.01)
*C07C 235/00* (2006.01)
*C07C 237/00* (2006.01)
*C07C 239/00* (2006.01)

(52) U.S. Cl. ..................................................... 564/161
(58) Field of Classification Search .................. 564/161
See application file for complete search history.

(56) References Cited

U.S. PATENT DOCUMENTS

| 5,034,541 A | 7/1991 | Bigg et al. |
| 5,136,082 A | 8/1992 | Dang et al. |
| 5,621,142 A | 4/1997 | Mochizuki et al. |
| 5,948,782 A * | 9/1999 | Sohda et al. ............. 514/266.1 |

FOREIGN PATENT DOCUMENTS

| EP | 0 747 348 A1 * | 12/1996 |
| EP | 1 845 084 A1 | 10/2007 |

OTHER PUBLICATIONS

Casidio, S. et al., "Acide phenyl-1-hydroxymethyl-2-cyclopropane carboxylique et derives", Bollettino Chimico Farmaceutico, vol. 117, No. 6, pp. 331-342, 1978, XP008085513. (with Summary).

* cited by examiner

*Primary Examiner*—Yvonne Eyler
*Assistant Examiner*—Kellette Gale
(74) *Attorney, Agent, or Firm*—Foley & Lardner LLP

(57) ABSTRACT

The present invention provides a process for producing (Z)-1-phenyl-1-diethylaminocarbonyl-2-hydroxymethylcyclopropane, which comprises reacting 2-oxo-1-phenyl-3-oxabicyclo[3.1.0]hexane with diethylamine in the presence of alkali metal alkoxide.

7 Claims, No Drawings

PROCESS FOR PRODUCING (Z)-1-PHENYL-1-DIETHYLAMINO CARBONYL-2-HYDROXYMETHYL CYCLOPROPANE

FIELD OF THE INVENTION

The present invention relates to a process for producing (Z)-1-phenyl-1-diethylaminocarbonyl-2-hydroxymethylcyclopropane that is an intermediate for producing (Z)-1-phenyl-1-diethylaminocarbonyl-2-aminomethylcyclopropane hydrochloride useful as an antidepressant.

BACKGROUND OF THE INVENTION (Z)-1-Phenyl-1-diethylaminocarbonyl-2-hydroxymethylcyclopropane is used as an intermediate for producing (Z)-1-phenyl-1-diethylaminocarbonyl-2-aminomethylcyclopropane hydrochloride that is known as an antidepressant having an activity of serotonin-noradrenalin reuptake inhibitor.

For synthesizing (Z)-1-phenyl-1-diethylaminocarbonyl-2-hydroxymethylcyclopropane, the process reacting 2-oxo-1-phenyl-3-oxabicyclo[3.1.0]hexane with diethylamine in the presence of butyllithium (refer, for example, EP0747348A; Shuto, S. et al., Journal of Medicinal Chemistry, 1995, Vol. 38, p. 2964-2968; Shuto, S. et al., Journal of Organic Chemistry, 1996, Vol. 61, No. 3, p. 915-923; Shuto, S. et al., Journal of Synthetic Organic Chemistry, Japan, 1997, Vol. 55, No. 10, p. 868-876; and Shuto, S. et al., Tetrahedron Letters, 1996, Vol. 37, No. 5, p. 641-644) or aluminum chloride (for example, U.S. Pat. No. 5034541) have been reported.

As the process using butyllithium, for example, EP0747348A discloses a process including a step of preparing lithium diethylamide by reacting butyllithium with diethylamine, and a step of reacting 2-oxo-1-phenyl-3-oxabicyclo[3.1.0]hexane as an raw material compound with the lithium diethylamide, resulting in production of (Z)-1-phenyl-1-diethylaminocarbonyl-2-hydroxymethylcyclopropane as an intended compound.

The process using bntyllithium, however, requires to conduct the reaction under an inert gas atmosphere such as argon at an ultra low temperature (−78° C.), causing a problem of troublesome operating procedures. Furthermore, butyllithium is so expensive that application of this process to industrial production has economical disadvantages.

On the other hand, as the process using aluminum chloride, for example, U.S. Pat. No. 5034541 discloses a process for producing (Z)-1-phenyl-1-diethylaminocarbonyl-2-hydroxymethylcyclopropane as an intended compound by a step of forming a complex of aluminum chloride as a Lewis acid and an amine, and a step of reacting 2-oxo-1-phenyl-3-oxabicyclo[3.1.0]hexane as a raw material compound with the complex and then amidating in a form of diethylamide.

This process, however, has a safety problem because of requiring halogen-system solvents, such as dichloroethane, which are highly toxic to human body.

SUMMARY OF THE INVENTION

The present invention intends to solve the above problems and to provide a process capable of producing (Z)-1-phenyl-1-diethylaminocarbonyl-2-hydroxymethylcyclopropane with a simple step but with more safety, lower cost, and higher yield than the conventional processes.

The inventors, after having diligently studied to solve the above problems, have achieved the present invention.

<1> A process for producing (Z)-1-phenyl-1-diethylaminocarbonyl-2-hydroxymethylcyclopropane, which comprises reacting 2-oxo-1-phenyl-3-oxabicyclo[3.1.0]hexane with diethylamine in the presence of alkali metal alkoxide.

<2> The process according to <1>, wherein the reaction is carried out in a solvent.

<3> The process according to <1>, wherein the alkali metal alkoxide is sodium methoxide or potassium methoxide.

<4> The process according to <2>, wherein the alkali metal alkoxide is sodium methoxide or potassium methoxide.

<5> The process according to <2> or <4>, wherein the solvent is methanol.

<6> The process according to any of <1> to <5>, wherein the amount of diethylamine is 1 to 10 gram equivalent to 1 gram equivalent of 2-oxo-1 phenyl-3-oxabicyclo[3.1.0]hexane.

<7> The process according to any of <1> to <6>, wherein the amount of alkali metal alkoxide is 1 to 5 gram equivalent to 1 gram equivalent of 2-oxo-1-phenyl-3-oxabicyclo[3.1.0]hexane.

DESCRIPTION OF PREFERRED EMBODIMENTS

The process of the present invention, for example, may be carried out by mixing 2-oxo-1-phenyl-3-oxabicyclo[3.1.0]hexane, diethylamine, and alkali metal alkoxide. The order of mixing them is not limited, and may be sequentially or simultaneously.

2-oxo-1-phenyl-3-oxabicyclo[3.1.0]hexane, which is a raw material compound for producing (Z)-1-phenyl-1-diethylaminocarbonyl-2-hydroxymethylcyclopropane, is known in public and can be prepared, for example, by a process described in EP0747348A mentioned above.

The amount of diethylamine, in view of yield and productivity, is usually 1 to 10 gram equivalent, preferably 2 to 4 gram equivalent, to 1 gram equivalent of 2-oxo-1-phenyl-3-oxabicyclo[3.1.0]hexane.

Examples of the alkali metal alkoxides used in the present invention include alkali metal salts of alcohol having 1 to 4 carbon atoms such as lithium methoxide, sodium methoxide, potassium methoxide, lithium ethoxide, sodium ethoxide, potassium ethoxide, sodium t-butoxide, potassium t-butoxide, and the like, and sodium methoxide and potassium methoxide are preferred, and sodium methoxide particularly preferred.

The amount of the alkali metal alkoxide, in view of yield and productivity, is usually 1 to 5 gram equivalent, preferably 1.5 to 4 gram equivalent, to 1 gram equivalent of 2-oxo-1-phenyl-3-oxabicyclo[3.1.0]hexane.

The alkali metal alkoxide mentioned above is not limited in its form for usage, may be used in a solid or solution state. When being used in a solution form, preferable is a solution of an alcohol solvent corresponding to the alkali metal alkoxide to be used (for example, sodium methoxide in methanol), and this alcohol solvent used is counted as a portion of the whole reaction solvent.

The reaction according to the present invention may be carried out, for example, in a solvent. The solvent to be used may be appropriately selected as long as not harming the reaction, may include, for example, alcohol solvents such as methanol and ethanol, and the like; aromatic hydrocarbon solvents such as toluene, and the like; and saturated hydrocarbon solvents such as hexane, heptane, and the like. These solvents may be used independently or as a combination of 2 or more kinds thereof.

The amount of the solvent is usually 1 to 10 ml, preferably 3 to 5 ml, to 1 g of 2-oxo-1-phenyl-3-oxabicyclo[3.1.0]hexane.

The reaction temperature is usually 0 to 100° C., preferably 20 to 80° C., particularly preferably 20 to 30° C.; the reaction time is, depending on the reaction volume, usually 3 to 30 hours.

The completion of the reaction can be confirmed by disappearance of, a raw material, 2-oxo-1-phenyl-3-oxabicyclo [3.1.0]hexane.

After the completion of the reaction, (Z)-1-phenyl-1-diethylaminocarbonyl-2-hydroxymethylcyclopropane, the intended compound, may be isolated by any of purification methods known by a person skilled in the art, such as high-performance liquid chromatography, distillation under reduced pressure, re-crystallization, and the like, or an appropriate combination thereof.

The (Z)-1-phenyl-1-diethylaminocarbonyl-2-hydroxymethylcyclopropane obtained can be introduced to (Z)-1-phenyl-1-diethylaminocarbonyl-2-aminomethylcyclopropane hydrochloride, an antidepressant, by a method, for example, described in EP0747348A mentioned above.

The invention will be explained in more detail according to Example, but should not be limited thereto.

REFERENTIAL EXAMPLE 1

Production of 2-oxo-1-phenyl-3-oxabicyclo[3.1.0]hexane

In a mixed solvent of toluene (26.0 kg) and N,N'-dimethyl-2-imidazolidinone (94.9 kg), 60% sodium hydride (27.2 kg, 683 mol) was added, and phenylacetonitrile (40.2 kg, 343 mol) was subsequently added dropwise therein at 10 to 20° C. After being stirred for 2 hours, a mixture of epichlorohydrin (31.7 kg, 343 mol) and toluene (26.0 kg) was added dropwise therein at 10 to 20° C. and then stirred. After confirming the disappearance of the raw material, methanol (22.0 kg) and water (120.6 kg) were added therein to be subjected to washing and phase separation.

The organic layer obtained was added with 24% aqueous solution of potassium hydroxide (159.1 kg) and tetrabutylammonium sulfate (1.1 kg) to be heated under refluxing. The organic phase was removed by a phase separation, and then further added with toluene (69.6 kg) and 35% hydrochloric acid (78.7 kg), followed by stirring at 60 to 70° C. for 2 hours. After the organic phase was separated by a phase separation, the organic phase was further washed twice with 8% aqueous sodium hydrogen carbonate solution and twice with water; and then the organic layer obtained was concentrated under a reduced pressure to obtain 40.7 kg of the titled compound in a form of light-yellow oily substance. Yield was 68.1%.

The obtained oily substance of 2-oxo-1-phenyl-3-oxabicyclo[3.1.0]hexane was cooled to transform to crystals.

EXAMPLE 1

Production of (Z)-1-phenyl-1-diethylaminocarbonyl-2-hydroxymethylcyclopropane

In a mixed solution of 2-oxo-1-phenyl-3-oxabicyclo[3.1.0] hexane (25.0 g, 0.144 mol) and toluene (20.0 g), diethylamine (31.5 g, 0.431 mol) was added, and then 28% sodium methoxide/methanol solution (83.1 g, 0.431 mol) was added dropwise therein at 20 to 30° C., and then stirred for 15 hours. At the time of completion of the stirring, the resultant reactant was analyzed with a high-performance liquid chromatography (HPLC: manufactured by Shimadzu Corporation, LC-10Avp, ODS column 4.6 mm×150 mm), resulting in a reaction rate of 91.3%. The reactant solution after finishing the stirring was added dropwise into a mixed solution of 27.5% aqueous solution of acetic acid solution (103.5 g) and toluene (50 ml) and subjected to a phase separation to remove a water layer. The organic layer remained washed with saline and dried with anhydrous magnesium sulfate. The solution obtained was dried to solidify under a reduced pressure to obtain 30.4 g of the intended compound as light yellow crystals. Yield was 87.0%.

Physical Properties: 1H-NMR (CDCl$_3$, 400 MHz): δ 0.89 (3H, t, J=7.0 Hz); 1.06 (1H, dd, J=5.2, 6.4 Hz); 1.12 (3H, t, J=7.0 Hz); 1.53 (1H, m); 1.63 (1H, dd, J=5.2, 8.8 Hz); 3.16 (1H, ddd, J=2.4, 10.0, 12.4 Hz); 3.34-3.54 (4H, m); 4.01 (1H, m); 4.71 (1H, d, J=11.2 Hz); 7.21-7.32 (5H, m)

EXAMPLE 2

Production of (Z)-1-phenyl-1-diethylaminocarbonyl-2-hydroxymethylcyclopropane

The reaction was carried out under the same conditions and procedures as in Example 1 except for using 2-oxo-1-phenyl-3-oxabicyclo[3.1.0]hexane (5.0 g, 0.029 mol), using sodium methoxide (3.0 equivalent to the raw material) instead of 28% sodium methoxide/methanol solution, and reacting at 60° C. The reaction rate analyzed with HPLC was 81.7%.

EXAMPLE 3

Production of (Z)-1-phenyl-1-diethylaminocarbonyl-2-hydroxymethylcyclopropane

The reaction was carried out under the same conditions and procedures as in Example 1 except for using 2-oxo-1-phenyl-3-oxabicyclo[3.1.0]hexane (5.0 g, 0.029 mol), using 28% sodium methoxide/methanol solution (3.0 equivalent to the raw material) without toluene solvent, and reacting at 20 to 30° C. The reaction rate analyzed with HPLC was 90.8%.

EXAMPLE 4

Production of (Z)-1-phenyl-1-diethylaminocarbonyl-2-hydroxymethylcyclopropane

The reaction was carried out under the same conditions and procedures as in Example 1 except for using 2-oxo-1-phenyl-3-oxabicyclo[3.1.0]hexane (5.0 g, 0.029 mol), using 28% sodium methoxide/methanol solution (1.5 equivalent to the raw material) without toluene solvent, and reacting at 60° C. The reaction rate analyzed with HPLC was 76.2%.

EXAMPLE 5

Production of (Z)-1-phenyl-1-diethylaminocarbonyl-2-hydroxymethylcyclopropane

The reaction was carried out under the same conditions and procedures as in Example 1 except for using 2-oxo-1-phenyl-3-oxabicyclo[3.1.0]hexane (5.0 g, 0.029 mol), using 28% sodium methoxide/methanol solution (3.0 equivalent to the raw material) without toluene solvent, and reacting at 60° C. The reaction rate analyzed with HPLC was 81.7%.

EXAMPLE 6

Production of (Z)-1-phenyl-1-diethylaminocarbonyl-2-hydroxymethylcyclopropane

The reaction was carried out under the same conditions and procedures as in Example 1 except for using 2-oxo-1-phenyl-3-oxabicyclo[3.1.0]hexane (5.0 g, 0.029 mol), using 28% sodium methoxide/methanol solution (4.0 equivalent to the raw material) without toluene solvent, and reacting at 60° C. The reaction rate analyzed with HPLC was 74.3%.

The process of the present invention is simpler than the conventional processes with requiring troublesome procedures, because inert gas atmosphere as well as ultra low temperature reaction condition is not required therefor.

The process of the present invention is also more economically advantageous than the conventional processes with using expensive butyllithium, because alkali metal alkoxides are used therefor.

The process of the present invention is further safer than the conventional processes, because halogen-system solvents highly toxic to human body are not used therefor.

The invention claimed is:

1. A process for producing (Z)-1-phenyl-1-diethylaminocarbonyl-2-hydroxymethylcyclopropane, which comprises reacting 2-oxo-1-phenyl-3-oxabicyclo[3.1.0]hexane with diethylamine in the presence of alkali metal alkoxide.

2. The process according to claim 1, wherein the reaction is carried out in a solvent.

3. The process according to claim 1, wherein the alkali metal alkoxide is sodium methoxide or potassium methoxide.

4. The process according to claim 2, wherein the alkali metal alkoxide is sodium methoxide or potassium methoxide.

5. The process according to claim 4, wherein the solvent is methanol.

6. The process according to claim 1, wherein the amount of diethylamine is 1 to 10 gram equivalent to 1 gram equivalent of 2-oxo-1-phenyl-3-oxabicyclo[3.1.0]hexane.

7. The process according to claim 1, wherein the amount of alkali metal alkoxide is 1 to 5 gram equivalent to 1 gram equivalent of 2-oxo-1-phenyl-3-oxabicyclo[3.1.0]hexane.

* * * * *

UNITED STATES PATENT AND TRADEMARK OFFICE
CERTIFICATE OF CORRECTION

PATENT NO. : 7,432,396 B2  Page 1 of 1
APPLICATION NO. : 11/630344
DATED : October 7, 2008
INVENTOR(S) : Yoshihide Niimoto and Hiroharu Kumazawa It is certified that error appears in the above-identified patent and that said Letters Patent is hereby corrected as shown below:

Title Page, Insert

-- (30)    Foreign Application Priority Data

Jun. 25, 2004    (JP) ...............................2004-188901 --

Signed and Sealed this

Second Day of December, 2008

JON W. DUDAS
*Director of the United States Patent and Trademark Office*